(12) United States Patent
Bartel

(10) Patent No.: US 6,464,703 B2
(45) Date of Patent: Oct. 15, 2002

(54) SURGICAL INSTRUMENT FOR MINIMALLY INVASIVE SURGERY

(75) Inventor: Volker Bartel, Bodelshausen (DE)

(73) Assignee: Elektromedizin GmbH, Tubingen (DE)

( * ) Notice: Subject to any disclaimer, the term of this patent is extended or adjusted under 35 U.S.C. 154(b) by 28 days.

(21) Appl. No.: 09/847,568

(22) Filed: May 2, 2001

(65) Prior Publication Data

US 2001/0041893 A1 Nov. 15, 2001

(30) Foreign Application Priority Data

May 4, 2000 (DE) ........................................ 100 21 724
Jun. 29, 2000 (DE) ........................................ 100 31 773

(51) Int. Cl.⁷ .............................................. A61B 18/18
(52) U.S. Cl. ................................. 606/51; 52/48; 52/46
(58) Field of Search ...................... 606/48, 46, 50–52, 606/45, 205, 207; 600/564, 562, 567

(56) References Cited

U.S. PATENT DOCUMENTS

| 5,172,700 | A |   | 12/1992 | Bencini et al. |
| 5,961,514 | A | * | 10/1999 | Long et al. ..................... 606/41 |
| 6,001,096 | A | * | 12/1999 | Bissinger et al. ........... 606/170 |
| 6,024,741 | A | * | 2/2000 | Williamson et al. .......... 606/40 |
| 6,273,887 | B1 | * | 8/2001 | Yamauchi et al. ............. 606/48 |
| 6,334,860 | B1 | * | 1/2002 | Dorn ............................. 606/48 |

FOREIGN PATENT DOCUMENTS

| DE | 25 19 827 |      | 11/1976 |
| DE | 39 17 328 | C2   | 11/1990 |
| DE | 40 32 471 | C2   | 4/1992 |
| DE | 195 37 320 | A1  | 4/1997 |
| DE | 197 31 884 | C1  | 7/1997 |

* cited by examiner

Primary Examiner—Roy D. Gibson
Assistant Examiner—Pete J Vrettakos
(74) Attorney, Agent, or Firm—Marshall, Gerstein & Borun

(57) ABSTRACT

The invention relates to a surgical instrument for minimally invasive surgery, in particular in the form of pincers or forceps. The instrument comprises at least two gripping elements, which for the purpose of gripping can be moved like forceps towards one another in a gripping direction or apart from one another in the opposite direction. At least one gripping element comprises at one end a first limb and a second limb, and at least one flexible bending region. The limbs are spaced apart from one another in the gripping direction with at least the first limb of each gripping element disposed within a guide sleeve and movable in a longitudinal direction of the guide sleeve, relative to the second limb of the gripping element in such a way that during a relative movement of the limbs with respect to one another the associated gripping element can be moved in the gripping direction.

14 Claims, 3 Drawing Sheets

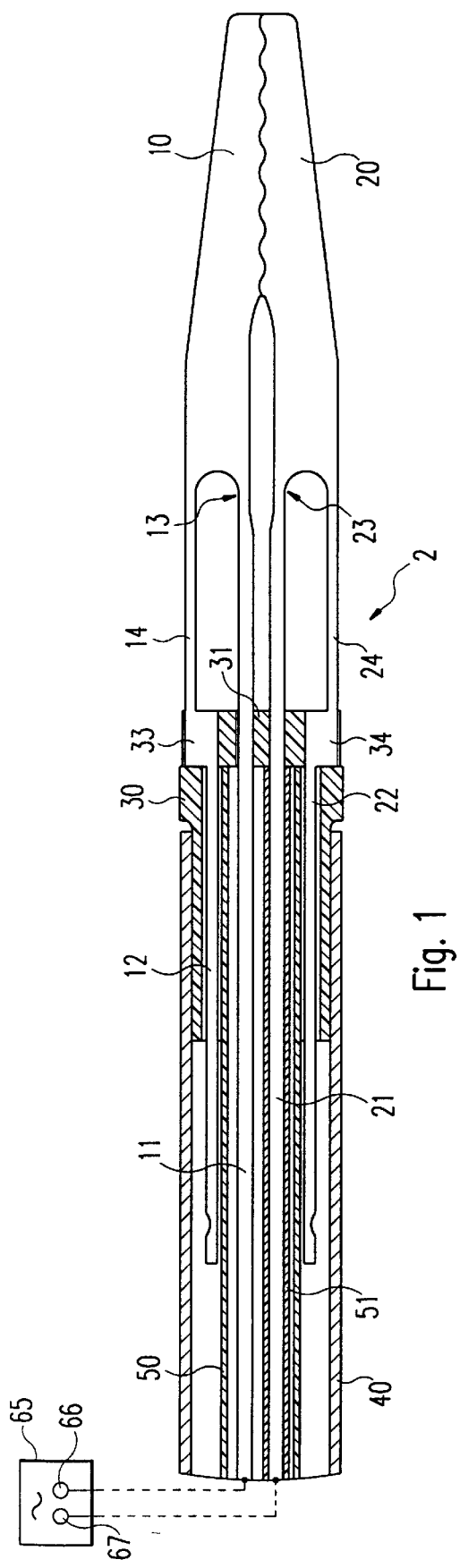
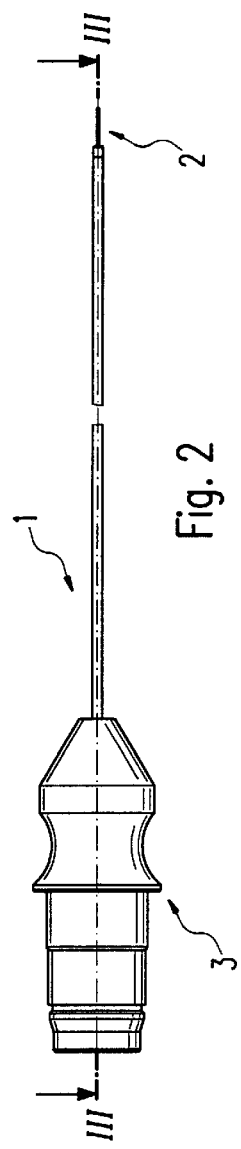
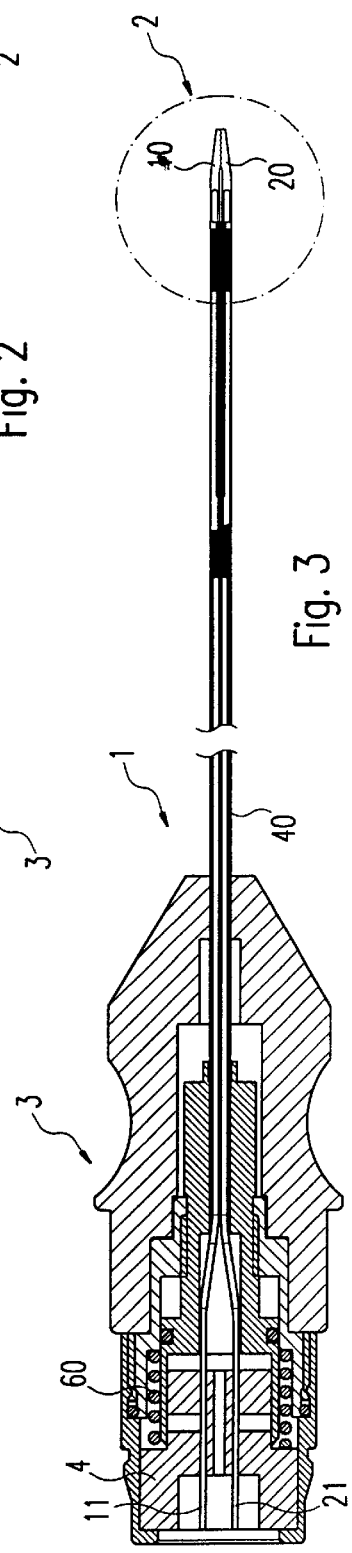
Fig. 1
Fig. 2
Fig. 3

SURGICAL INSTRUMENT FOR MINIMALLY INVASIVE SURGERY

FIELD OF THE INVENTION

The present invention relates to a surgical instrument for minimally invasive surgery and in particular an instrument in the form of a pair of pincers or forceps.

Surgical instruments of this kind are used for minimally invasive surgery in order, for example, to grasp tissue, small blood vessels and similar biological materials. Like a pair of pincers or forceps, such an instrument comprises movable gripping elements that can be brought together or spread apart, i.e. closed by movement in a gripping direction or opened by movement in the opposite direction. Because of their small dimensions, the instruments can preferentially be used in the working channel of an endoscope.

DESCRIPTION OF THE PRIOR ART

The German patent DE 195 37 320 A1 discloses an apparatus for actuating a gripping device for minimally invasive surgery, in which the device resembles forceps in having two movable gripping elements, each in the form of one member of a pair of forceps. The gripping elements are connected to a first and a second holder element, respectively, in each case by way of two flexible connecting elements. In order to spread the two movable manipulation elements apart, or to bring them together, the two holder elements are displaced with respect to one another. An advantage of this apparatus is stated to be that on one hand it comprises no joints that would be subject to wear and tear, while on the other hand it can be manufactured from a single blank of material.

However, this specification does not provide for the said apparatus to be used in minimally invasive surgery in order to coagulate biological tissue, for instance as a bipolar instrument.

In DE 40 32 471 C2 is disclosed an electrosurgical apparatus that can be used either for bipolar coagulation or for separating tissues, as desired, and which comprises three mutually insulated contact rods mounted in an elongated instrument casing. Two of the contact rods have free ends that serve as coagulation electrodes, while the third contact rod acts a cutting electrode. For this purpose the third contact rod can be moved towards the two coagulation electrodes or through these electrodes, so that tissue that is to be coagulated or cut can be clamped between the electrodes as though in a pair of forceps.

DE 39 17 328 C2 discloses a bipolar coagulation instrument with two mutually insulated and movable mouth elements that together form a pair of forceps. In this case a first mouth element is fixed and the second mouth element can be moved with respect to the first mouth element.

Both of the instruments or apparatuses mentioned above are relatively elaborate in construction and hence are correspondingly expensive to manufacture.

The object of the present invention is to provide a surgical instrument, in particular pincers or forceps for minimally invasive surgery, that has a simple structure and as a result can be constructed with a very small diameter.

SUMMARY OF THE INVENTION

According to the present invention there is provided a surgical instrument for minimally invasive surgery comprising at least two gripping elements, that can be moved in the manner of forceps towards one another in a gripping direction for the purpose of gripping and apart from one another in an opposite direction, at least one of the gripping elements comprising at one end thereof a first limb and a second limb, which limbs are spaced from one another in the gripping direction and which limbs each comprise at least one flexible region; and a guide sleeve in which at least the first limb of said one gripping element is disposed and can be moved in a longitudinal direction of the guide sleeve relative to the second limb of said one gripping element in such a way that during a relative movement of the first and second limbs with respect to one another said one gripping element is moved in the gripping direction.

It will be appreciated that the limbs bend at their flexible regions when the two limbs of a given gripping element are shifted relative to one another. In principle the instrument is also suitable for use as scissors, when the gripping elements are provided with cutting blades. For example, one edge of at least one gripping element can be sharpened for cutting.

In a preferred embodiment, so that the gripping elements can be moved apart from one another the first limb, for example, of each gripping element is moved in the longitudinal direction of the guide sleeve, towards the gripping end of the gripping element. Because of the torque thus produced, the limbs bend in their flexible region in such a way that the gripping elements are spread apart, moving in the direction opposite to the gripping direction. When the first limbs are moved back, the gripping elements again fold together because of the restoring force of the flexible regions or a corresponding oppositely directed movement of the limbs, as a result of which tissue situated between the gripping elements can be securely grasped. On the whole the instrument is of simple construction, which allows its size to be made particularly small.

In a preferred embodiment, the gripping elements themselves are made of a conductive material, in particular a metal and preferably stainless steel. The gripping elements are preferably so disposed that the limbs do not touch one another and hence are electrically isolated from one another. As a result, the gripping elements are suitable for use as electrodes for the coagulation of biological tissue.

Preferably, each gripping element including both of its limbs is produced as an integral component made of a conductive, in particular metallic material. As a result the gripping elements can be very inexpensively manufactured; it is also possible to make them of conductive plastic or similar conductive materials.

Preferably, the first limb of each gripping element is longer than the second limb, so that the gripping elements can be actuated directly by way of the first limb, i.e. without joints, connecting rods, shafts or similar devices, and with no play whatsoever. In addition, the first limbs can be used directly as conductors of a current for HF coagulation. As a means of actuating the gripping elements, for example, a rod can be welded to the first limb of each element. This enables the actuation to be done at a great distance from the gripping elements.

A further simplification in production of the instrument is achieved in a preferred embodiment by fixing the second limb of each gripping element firmly, in particular to the internal wall of the guide sleeve, for example by a form-fitting connection. Such a design is less expensive in terms of manufacturing technology and requires less space than a screw connection.

In order to supply a high-frequency coagulation current to a tissue grasped by the instrument, the limbs of the various gripping elements are electrically insulated from one another, and in particular are enclosed in an insulating sheath. So that short-circuits are reliably avoided, the limbs of the gripping elements are preferably enclosed in an insulating sheath before installation in the guide sleeve. With such insulation there is no longer any need to be concerned with production tolerances, as a result of which limbs of different gripping elements might come into contact with one another.

For manipulation of the instrument, the guide sleeve is partially inserted into one end of a flexible or in particular metallic tube. The tube can be made in particular of stainless steel corresponding to the types of stainless steel employed in surgery. A flexible or rigid tube facilitates manipulation of the instrument and above all provides good protection against contamination with dirt, and can be more easily cleaned and sterilized for surgical interventions.

Preferably the flexible or rigid tube is provided at the end opposite the guide sleeve with a controllable actuator or a handle to manipulate the instrument, in particular to actuate the gripping elements, i.e. to move them apart from one another or bring them together. The handle enables the surgical instrument to be simply and conveniently manipulated by an operator.

In a further embodiment of the handle the first limbs of the gripping elements are connected to an actuator disposed in the handle in such a way that when the actuator is pushed into the handle, the first limbs are moved away from the handle in the longitudinal direction of the guide sleeve and the flexible or rigid tube, as a result of which the gripping elements move apart from one another, in the direction opposite to the gripping direction. Conversely, the gripping elements move back together, in the gripping direction, when the actuator is moved or pulled out of the handle and hence the first limbs are pulled back again.

Between actuator and handle a spring is preferably disposed, so that with no need for the action of external force the actuator is pressed out of the handle and the gripping elements are brought together; this corresponds, so to speak, to the resting position of the instrument. Then in order to grasp tissue an operator must merely press the actuator into the handle, so that the gripping elements are spread apart, and when they have enclosed the tissue the actuator is released again, whereupon it is pressed back into its starting position by the force of a spring, so that the gripping elements come together and grip the tissue firmly with a specific force.

For use as a bipolar instrument for HF coagulation, in a preferred embodiment the first limb of a first gripping element can be connected to a first connector of a HF current generator and the first limb of a second gripping element, to a second connector thereof. The first and the second gripping elements then correspond to two electrodes of opposite polarity, and they serve to conduct HF current to a tissue that is grasped by both gripping elements.

The invention further relates to the use of the instrument in an endoscope. For this purpose the instrument is preferably movably disposed in the working channel of the endoscope and can be moved out of the endoscope in order to grasp, cut, spread apart and/or coagulate tissue, during which processes the endoscope allows the operator to monitor the instrument visually.

The invention will now be described by way of example with reference to the accompanying drawings.

BRIEF DESCRIPTION OF THE DRAWINGS

FIG. 1 is a side view, in partial longitudinal section, of a first embodiment of surgical instrument in accordance with the invention;

FIG. 2 is a side view of a handle and an actuator for the instrument shown in FIG. 1;

FIG. 3 is a longitudinal section along the line III—III in FIG. 2;

DESCRIPTION OF THE PREFERRED EMBODIMENTS

Figure 6:
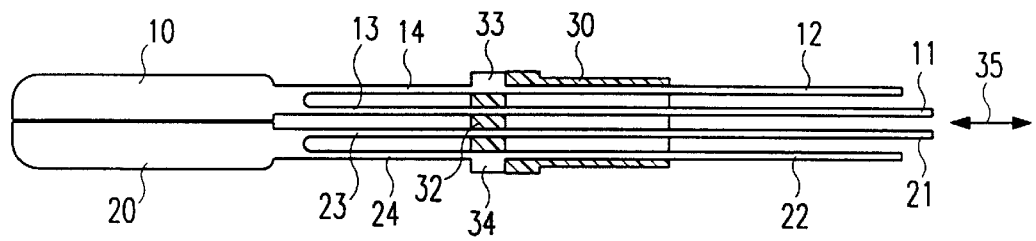
FIG. 6 is a part sectional view along the line VI—VI in FIG. 5.

In the following description, the same reference numerals are used for identical parts or parts with identical actions.

In FIG. 1 the tip 2 of a first exemplary embodiment of the surgical instrument in accordance with the invention is shown. Two gripping elements 10 and 20 are disposed within a guide sleeve 30, which in turn is partially inserted into one end of a tube 40, which may be flexible but is preferably metallic. The tube 40 serves on one hand as a protective outer sheath and on the other hand as a guide for the instrument tip. The guide sleeve 30 consists preferably of an insulating material, in particular a plastic. The guide sleeve 30 guides first or inner limbs 11 and 21 as well as second or outer limbs 12 and 22 of the first and second gripping elements 10 and 20, respectively. Limbs and gripping elements are each constructed in one piece of a conductive material, in particular a stainless steel such as Nitinol (NiTi). Nitinol is more extensible than steel, 8% as opposed to only 0.2%, and is thus particularly suitable for the limbs. At their ends facing away from the limbs, the two gripping elements 10 and 20 are constructed similarly to the jaws of pliers and, in particular, in the juxtaposed state they fit together in such a way that the profiling of a gripping surface of the first gripping element 10 intermeshes with a complementary profiling of a gripping surface of the second gripping element 20.

The sections of the first limbs 11 and 21 that are outside the guide sleeve 30 and metal tube 40, as well as the corresponding sections of the second limbs 12 and 22, each comprise a flexible region 13 or 23 and 14 or 24, respectively. When the gripping elements are made of metal, the flexible regions are springy. The second limbs 12 and 22 of the first gripping element 10 and second gripping element 20, respectively, are firmly attached to the guide sleeve 30, in particular are fixed by adhesive or by clamping, and are prevented from moving into the guide sleeve 30 by projections 33, 34. The first limb 11 of the first gripping element 10 and first limb 21 of the second gripping element 20 are each movably mounted in the guide sleeve 30 and are separated from one another by means of an isolating spacer 31 (which forms part of the guide sleeve 30). For supplementary isolation the first limbs 11 and 21 are each enclosed in an insulating sheath 51. To ensure that during assembly of the instrument adhesive is prevented from coming into contact with the movable parts, in particular the first limbs 11 and 21, an additional tube 50 is provided as a protective sheath. For this purpose the tube 50 surrounds the movable first limbs 11 and 12.

To the two first limbs 11 and 21 is attached a HF current generator 65 that can provide a high-frequency coagulation current. For this purpose the first limb 11 is connected to a first connector 66 of the HF current generator 65. The first limb 21 of the second gripping element 20 is connected to a second connector 67 of the generator 65. Because of the insulating properties of the structure guiding the first limbs 11 and 21, the gripping elements 10 and 20 are completely electrically isolated from one another until they emerge from the guide sleeve 30. When the gripping elements are in juxtaposition with nothing between them, the gripping surfaces can touch one another so that an electrical contact is created between the two gripping elements 10 and 20. For the purpose of coagulation, tissue is grasped between the two gripping elements, so that a corresponding coagulation current flows from one gripping element through the tissue and into the other gripping element.

The function of the instrument tip 2 is explained in greater detail with reference to the following figures.

FIG. 2 shows a complete side view of the surgical instrument 1 with instrument tip 2 and a handle 3.

In FIG. 3 is shown a longitudinal section, along the line III—III, through the surgical instrument 1 according to FIG. 2. In this longitudinal section the structure of the handle 3 and in particular the way it functions can be seen.

The first limbs 11 and 21 extending back from the gripping elements 10 and 20, respectively, pass through the tube 40 into an actuator 4, which is reciprocatingly mounted within the handle 3 and serves to move the gripping elements 10 and 20 apart from one another, against the gripping direction, or to bring them together in the gripping direction. By means of a coil spring 60 the actuator 4 is pressed out of the handle until it abuts against a stop, as a result of which a pulling force is exerted upon the first limbs 11 and 21 of the gripping elements 10 and 20, specifically on the parts thereof that are fixed within the actuator 4; this force is exerted in the longitudinal direction of the tube 40 and the guide sleeve 30, so that the gripping elements 10 and 20 are brought together and the projections 33, 34 of the outer limbs 12, 22 are apposed to the sleeve 30. This corresponds, so to speak, to the resting position of the instrument.

By applying pressure to the actuator 4, more particularly by pushing the actuator 4 into the handle 3 so as to compress the coil spring 60, a pushing force is exerted on the first limbs 11 and 21, as a result of which the first limbs 11 and 21 are pushed or pressed away from the handle 3 in the long direction of the tube 40 and guide sleeve 30. At the tip 2 of the instrument this produces a torque about the point where the second limbs 12 and 22 are fixed to the guide sleeve 30, so that the gripping elements 10 and 20 that extend out of the guide sleeve 30 at the instrument tip 2 are bent outward at their flexible regions 13, 14 and 23, 24, as a result of which the gripping elements 10 and 20 move apart from one another against the gripping direction. Now tissue can be enclosed by the two gripping elements 10 and 20 and be grasped and when the pressure is removed from the actuator 4. In the absence of this manipulation pressure, the coil spring 60 presses the actuator 4 back out of the handle 3, whereupon a pulling force is exerted on the first limbs 11 and 21 and causes the gripping elements 10 and 20 to move together in the gripping direction and hold or grasp the tissue. The tissue is thus clamped between the two gripping surfaces of the gripping elements. If the limbs are pre-curved in the opening direction of the gripping elements (see FIG. 7), given a suitable dimensioning of the coil spring the entire arrangement can be held together even without adhesive, by the pretensioning so produced.

Figure 4:
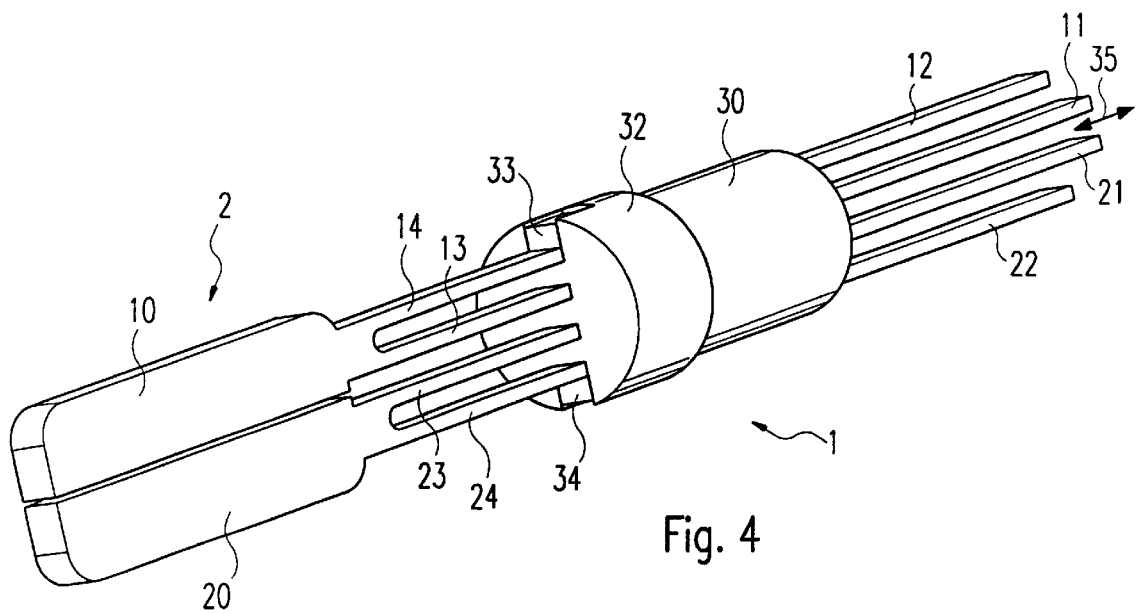
FIG. 4 is a perspective view of a second embodiment of surgical instrument in accordance with the invention, shown with gripping elements juxtaposed.

FIG. 4 shows a perspective view of a second exemplary embodiment of the surgical instrument in accordance with the invention, with gripping elements juxtaposed. In contrast to the first exemplary embodiment, only the two gripping elements 10 and 20, a guide sleeve 30 and its cap section 32 are shown. Furthermore, the gripping surfaces of the two gripping elements 10 and 20 are smooth, i.e. not profiled.

The first, inner limbs 11 and 21 as well as the second, outer limbs 12 and 22 of the gripping elements 10 and 20 are disposed completely within the guide sleeve, which substantially prevents soiling or contamination and ensures precise guidance. However, because it cannot be excluded that the instrument may be dirtied by fluids, blood or similar substances that enter by capillary action, the instrument is provided with a rinsing channel for cleaning.

The second limbs 12 and 22 comprise projections 33 and 34 that prevent the second limbs 12 and 22 from moving into the guide sleeve in the long direction. The projections 33 and 34 are disposed in recesses within the cap section 32 that are provided for that purpose, so that rotation of the gripping elements 10 and 20 within the guide sleeve 30 is likewise prevented. The projections also serve to fix the second limbs 12 and 22 to the guide sleeve 30. For this purpose the projections 33 and 34 can additionally, for example, be glued to the guide sleeve 30 and/or covering cap 32 or can be clamped into the recesses in the covering cap 32.

Figure 5:
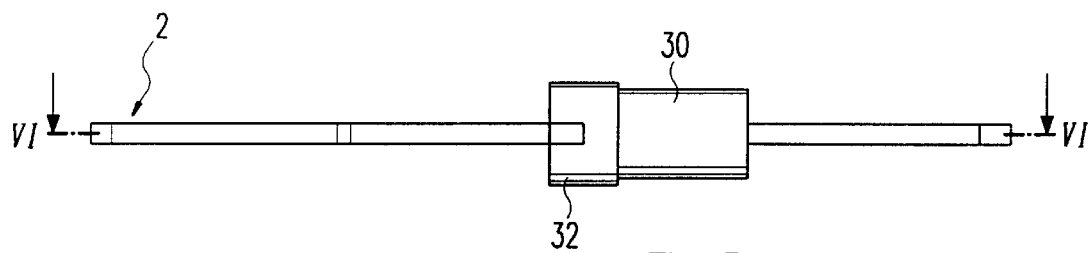
FIG. 5 is a side view of the surgical instrument shown in FIG. 4.

FIG. 5 is a side view of the second exemplary embodiment of the surgical instrument, as shown in FIG. 4.

FIG. 6 shows a partial section along the line VI—VI of the exemplary embodiment according to FIG. 5. The guide sleeve 30 is made of an insulating material, in particular a plastic. The first, inner limbs 11 and 21 of the two gripping elements 10 and 20 are made longer than the second, outer limbs 12 and 22. The projections 33 and 34 of the second limbs 12 and 22 of the two gripping elements 10 and 20, respectively, abut against the guide sleeve 30 in such a way that they cannot be moved into the guide sleeve.

In order to move the gripping elements 10 and 20 apart from one another or bring them together, the longer, first limbs 11 and 21 are moved in the direction indicated by the double-headed arrow 35.

Figure 7:
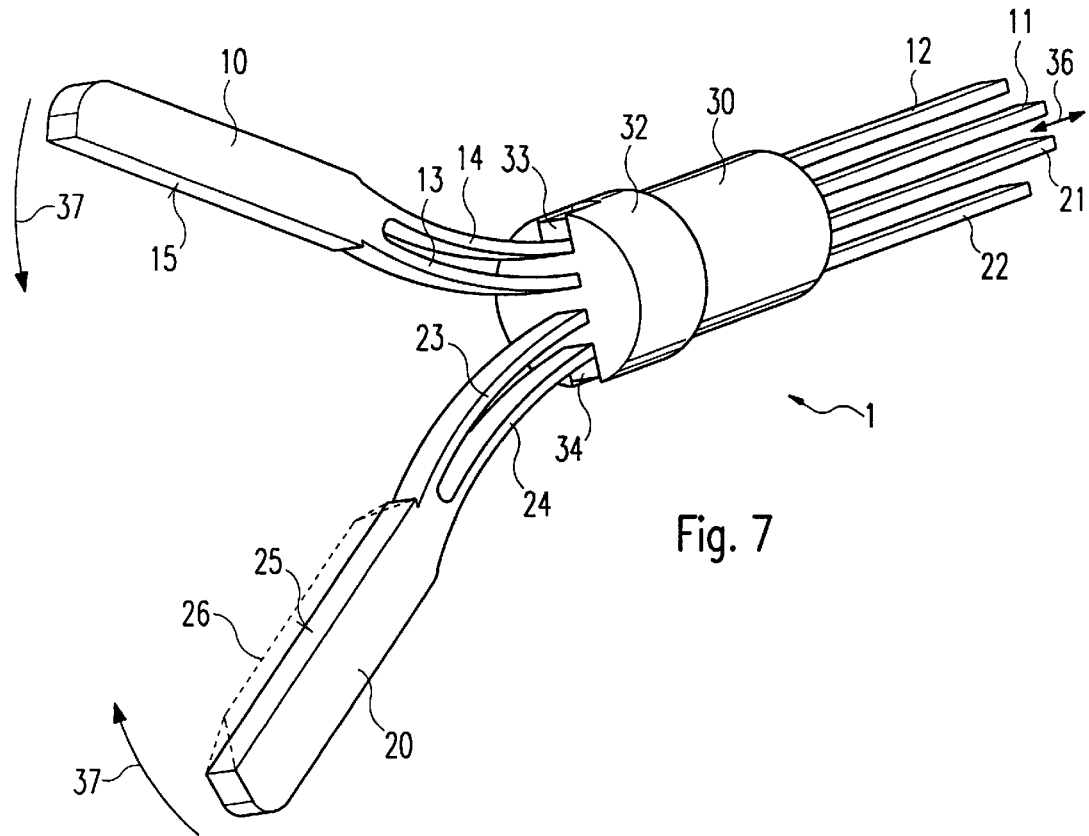
FIG. 7 is a perspective view of the instrument shown in FIG. 4, with gripping elements spread apart.

FIG. 7 shows the exemplary embodiment of the instrument represented in FIG. 4 with gripping elements bent apart, as a result of the pre-curvature of the limb sections 13, 14, 23, 24. That is, in the resting position the gripping elements of the instrument are opened outward. In order to bring the gripping elements together, the two inner or first limbs 11 and 21 are moved in the direction of the arrow 36. This movement produces a torque about the fixed second limbs 12 and 22, as a result of which the gripping elements 10 and 20 bend at the flexible regions 13, 14 and 23, 24 of the limbs 11 and 12 or 21 and 22, respectively, so that the gripping elements 10 and 20 come together in the gripping direction 37. Easily discernible are the gripping surfaces 15 and 25 of the first and second gripping elements 10 and 20, respectively. If at least one of the two gripping surfaces 15 or 25 is constructed as a cutting blade, the instrument 1 can also be used to cut tissue or can be employed as scissors. In FIG. 7 the construction of the gripping surface 25 as cutting blade 26 is indicated by the dashed lines.

Figure 9:
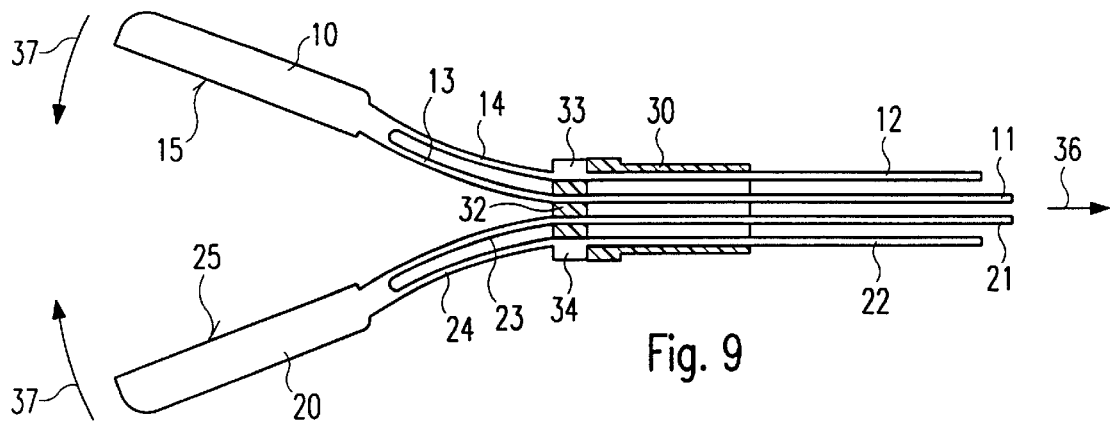
FIG. 9 is a part sectional view along the line IX—IX in FIG. 8.
Figure 8:
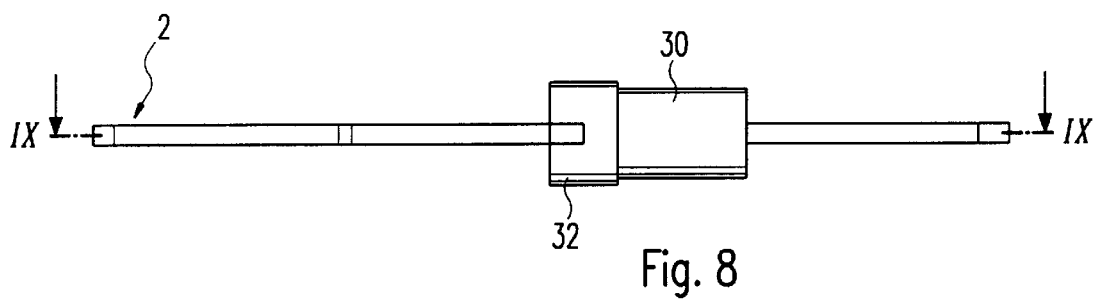
FIG. 8 is a side view of the instrument shown in FIG. 7.

Finally, FIG. 8 is a side view of the instrument shown in FIG. 7 and FIG. 9 shows a section along the line IX—IX of the instrument according to FIG. 8.

What is claimed is:

1. A surgical instrument for minimally invasive surgery comprising
   at least two gripping elements, that can be moved in the manner of forceps towards one another in a gripping direction for the purpose of gripping and apart from one another in an opposite direction, at least one of the gripping elements comprising at one end thereof a first limb and a second limb, which limbs are spaced from one another in the gripping direction and which limbs each comprise at least one flexible region; and
   a guide sleeve in which at least the first limb of said one gripping element is disposed and can be moved in a longitudinal direction of the guide sleeve relative to the second limb of said one gripping element in such a way that during a relative movement of the first and second limbs with respect to one another said one gripping element is moved in the gripping direction.

2. A surgical instrument as claimed in claim 1, wherein the second limb of the gripping element is fixed to the guide sleeve.

3. A surgical instrument as claimed in claim 1, wherein each gripping element, including its limbs, is constructed in one piece from a conductive, metallic material.

4. A surgical instrument as claimed in claim 1, wherein the first limb of each gripping element is longer than the second limb of the gripping element.

5. A surgical instrument as claimed in claim 1, wherein the second limb of each gripping element is connected to an interior wall defined by the guide sleeve.

6. A surgical instrument as claimed in claim 1, wherein the second limb of each gripping element is secured by an adhesive to an interior wall defined by the guide sleeve.

7. A surgical instrument as claimed in claim 1, wherein each of the gripping elements comprises first and second limbs, the first limbs of each of the gripping elements being electrically insulated from one another.

8. A surgical instrument as claimed in claim 1, comprising a tube into one end of which the guide sleeve is partially inserted.

9. A surgical instrument as claimed in claim 8, wherein the tube is provided with at its end opposite said one end with a handle by means of which the instrument can be manipulated.

10. A surgical instrument as claimed in claim 9, comprising an actuator reciprocatingly mounted in the handle and wherein each of the gripping elements comprises first and second limbs, the first limbs of the gripping elements being connected to the actuator in such a way that when the actuator is moved into the handle, the first limbs are moved in a longitudinal direction of the guide sleeve and the tube away from the handle so that the gripping elements bend apart from one another, and when the actuator is moved in a longitudinal direction of the guide sleeve and the tube towards the handle, the first limbs are moved in a longitudinal direction of the guide sleeve and the tube towards the handle so that the gripping elements are moved towards one another.

11. A surgical instrument as claimed in claim 10, wherein a tensioning device is disposed between the actuator and the handle so that with no application of external force the actuator is pressed against the handle and the gripping elements are brought together.

12. A surgical instrument as claimed in claim 2, wherein the first limb is pulled into the guide sleeve by a tensioning device and a projection is provided at the second limb that prevents the second limbs and thereby the gripping element from moving into the guide sleeve.

13. A surgical instrument as claimed in claim 1, comprising a HF current generator and wherein the first limb of a first gripping element is adapted for connection to a first connector of the generator and the first limb of a second gripping element is adapted for connection to a second connector of the generator.

14. The use of a surgical instrument for minimally invasive surgery as claimed in claim 1 when in a working channel of an endoscope.

* * * * *